(12) United States Patent
Schmidt

(10) Patent No.: US 8,735,635 B2
(45) Date of Patent: May 27, 2014

(54) PROCESS FOR MAKING 1, 2-PROPANE DIOL FROM HYDROGENATION OF GLYCEROL

(75) Inventor: Stephen Raymond Schmidt, Silver Spring, MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 97 days.

(21) Appl. No.: 13/203,264

(22) PCT Filed: Feb. 23, 2010

(86) PCT No.: PCT/US2010/024977
§ 371 (c)(1),
(2), (4) Date: Aug. 25, 2011

(87) PCT Pub. No.: WO2010/099078
PCT Pub. Date: Sep. 2, 2010

(65) Prior Publication Data
US 2011/0313211 A1    Dec. 22, 2011

Related U.S. Application Data

(60) Provisional application No. 61/208,514, filed on Feb. 25, 2009.

(51) Int. Cl.
*C07C 27/00* (2006.01)

(52) U.S. Cl.
USPC ........................................................ 568/861

(58) Field of Classification Search
None
See application file for complete search history.

(56) References Cited

U.S. PATENT DOCUMENTS

| | | | |
|---|---|---|---|
| 1,628,190 A | 5/1927 | Raney | |
| 1,915,473 A | 6/1933 | Raney | |
| 2,139,602 A | 12/1938 | Raney | 23/238 |
| 2,461,396 A | 2/1949 | Raney | 75/0.5 |
| 2,977,327 A | 3/1961 | Raney | 252/472 |
| 3,839,011 A | 10/1974 | Larson | 75/0.5 |
| 3,929,673 A | 12/1975 | Hoffman et al. | 252/463 |
| 3,953,367 A | 4/1976 | Hoffman et al. | 252/463 |
| 4,175,954 A | 11/1979 | Oden et al. | 75/138 |
| 5,063,189 A | 11/1991 | Jowett et al. | 502/150 |
| 5,214,219 A * | 5/1993 | Casale et al. | 568/861 |
| 5,616,817 A | 4/1997 | Schuster et al. | 568/861 |
| 5,801,286 A | 9/1998 | Besson et al. | 564/490 |
| 6,284,703 B1 | 9/2001 | Ostgard et al. | 502/301 |
| 6,395,403 B2 | 5/2002 | Schmidt | 428/570 |
| 6,429,337 B1 | 8/2002 | Schmidt | 564/423 |
| 6,486,366 B1 | 11/2002 | Ostgard et al. | 568/863 |
| 6,573,213 B1 | 6/2003 | Ostgard et al. | 502/301 |
| 6,747,180 B2 | 6/2004 | Ostgard et al. | 585/250 |
| 6,794,331 B2 | 9/2004 | Ostgard et al. | 502/301 |
| 6,995,107 B2 | 2/2006 | Shimazu et al. | 502/25 |
| 7,094,729 B2 | 8/2006 | Adkins et al. | 502/301 |
| 7,355,083 B2 | 4/2008 | Tuck et al. | |
| 7,375,053 B2 | 5/2008 | Schmidt | 502/326 |
| 2001/0018402 A1 | 8/2001 | Ostgard et al. | 502/345 |
| 2002/0037808 A1 | 3/2002 | Ostgard et al. | 502/301 |
| 2002/0038051 A1 | 3/2002 | Ostgard et al. | 562/538 |
| 2002/0151436 A1 | 10/2002 | Ostgard et al. | 502/301 |
| 2002/0193618 A1 | 12/2002 | Ostgard et al. | |
| 2003/0040433 A1 | 2/2003 | Case | B01J 25/00 |
| 2003/0120116 A1 | 6/2003 | Ostgard et al. | B01J 25/02 |
| 2003/0125200 A1 | 7/2003 | Ostgard et al. | B01J 25/00 |
| 2003/0203812 A1 | 10/2003 | Ostgard et al. | B01J 25/00 |
| 2003/0211938 A1 | 11/2003 | Ostgard et al. | B01J 23/40 |
| 2004/0074571 A1 | 4/2004 | Adkins et al. | B01J 25/00 |
| 2004/0199007 A1 | 10/2004 | Ostgard et al. | 562/539 |
| 2004/0260120 A1 | 12/2004 | Ostgard et al. | 562/538 |
| 2007/0270306 A1 | 11/2007 | Ostgard et al. | 502/301 |
| 2008/0045749 A1 | 2/2008 | Arredondo et al. | |
| 2008/0194401 A1 | 8/2008 | Schmidt | |

FOREIGN PATENT DOCUMENTS

| | | | |
|---|---|---|---|
| DE | 524101 | 5/1931 | |
| EP | 0523015 | 1/1993 | ............... C07C 31/20 |
| WO | 2007099161 | 9/2007 | ............... C07C 29/60 |

OTHER PUBLICATIONS

C. Montassier et al., In Bulletin De La Societe Chimique De France vol. 1989, Issue No. 2, pp. 148-155.
R. Connor and H. Adkins In J. Am. Chem. Soc. 54, 1932, pp. 4678-4690.
M. A. Dasari et al., In Appl. Chem. A: General 281, 2005, pp. 225-231.
J. Chaminand et al., In Green Chem. 6, 2004, pp. 359-361.

\* cited by examiner

*Primary Examiner* — Sudhakar Katakam
(74) *Attorney, Agent, or Firm* — Charles A. Cross

(57) ABSTRACT

This invention is a process for making 1,2-propane diol from glycerol. The process comprises subjecting a glycerol stream to hydrogenation conditions in the presence of a transition metal promoted skeletal copper catalyst to enhance selective production of 1,2-propane diol product. Chromium promoted catalyst is preferred for this invention, and moreover, it is preferred that the skeletal copper catalyst is prepared from copper aluminum alloys that have been subjected to leaching conditions selected to achieve at least 40% leaching of aluminum from the alloy. This process is particularly conducive to conducting the hydrogenation with reactant mixture in the liquid phase. The catalysts used in this invention are particularly suitable for use in a fixed catalyst bed, but can be activated and sized so that the catalyst is also suitable for use in slurry based reactions.

18 Claims, 6 Drawing Sheets

PROCESS FOR MAKING 1, 2-PROPANE DIOL FROM HYDROGENATION OF GLYCEROL

RELATED APPLICATIONS

This application claims priority and the benefit of the filing date of U.S. Provisional Patent Application No. 61/208,514 filed Feb. 25, 2009, and International Application No. PCT/US10/024977 filed Feb. 23, 2010, the disclosures of which are hereby incorporated herein by reference.

FIELD OF THE INVENTION

This invention relates to the manufacture of 1,2-propane diol (also known as propylene glycol) from glycerol (glycerin) using copper-based hydrogenation catalysts.

BACKGROUND

As described in WO 2007/099161, glycerol is becoming an abundant chemical product as industry and consumers become increasingly reliant on fuels from biological sources. In particular, fuels (also known as biofuels) are being made from biogenic fat- or oil-containing sources and used oils obtained, for example, from cooking oil waste from restaurants and waste animal fats from food-related processing plants. Diminishing supply of readily available traditional petroleum sources, increasing prices of petroleum feeds and concerns of their impact on the environment are driving increased demands for alternative fuels such as biofuels.

Biogenic oils and fats as they exist per se are not particularly suitable as engine fuel, and therefore require further processing and purification using generally complex processes. These processes, for example, remove lectins, carbohydrates and proteins, also referred to as oil sludge. With some oils, such as rapeseed oil, large amounts of free fatty acids have to be removed.

Biogenic oils processed in this manner differ from conventional diesel fuels in several respects. The former typically have a higher density than diesel fuel, and the cetane number of certain biogenic oils, such as rapeseed oil, is lower than that of diesel fuel. The higher viscosity and lower cetane for these oils lead to an unacceptable deterioration in the oil's fuel properties, which can lead to an engine running less smoothly, thereby increasing noise emission, as well as lead to incomplete combustion in the engine's combustion chamber because of decreased atomization of a more viscous fuel. Incomplete combustion leads to coking, and therefore increased particulate emission.

The above problems can be solved by converting (via transesterification) triglycerides (fatty acid esters of glycerol) present in the biogenic oil and used fats into monoalkyl esters of fatty acids, in particular methyl or ethyl esters. These esters, also referred to as "biodiesel" or FAME, can be used to run diesel engines without major retrofits, and frequently at reduced particulate emissions compared to normal diesel fuel. Conversion of these of triglycerides via transesterification for biodiesel production does result in glycerol (~10%), however. Transesterification processes therefore can be inefficient due to conversion of the feedstock to a product with little industrial value. There is therefore a need for effective and economical processes, which permit utilization of the glycerol obtained in biodiesel production, especially on an industrial scale.

Processes for hydrogenation of glycerol into usable chemicals are known. Various catalysts have been utilized in these processes, and a number of these catalysts comprise copper.

J. Chaminand et al., in Green Chem. 6, 2004, pages 359-361, describe the hydrogenation of aqueous glycerol solutions at 180° C. and 80 bar hydrogen pressure in the presence of supported metal catalysts based on Cu, Pd and Rh. Copper chromite, copper zinc oxide, copper aluminum oxide and copper silicon dioxide are mentioned as catalysts for such processes. Indeed, it is widely known that copper chromite is a suitable catalyst in the hydrogenation of glycerol. Copper chromite, however, is an oxide that is prone to chemical and physical degradation relative to metallic catalysts.

M. A. Dasari et al., in Appl. Chem. A: General 281, 2005, pages 225-231, describe a process for the low-pressure hydrogenation of glycerol to propylene glycol (1,2-propane diol) at a temperature of 200° C. and a hydrogen pressure of 200 psi (13.79 bar) in the presence of a nickel, palladium, platinum, copper, or copper chromite catalyst.

German Patent 524 101 has been attributed as describing a process, in which glycerol is subjected to a gas-phase hydrogenation in the presence of a hydrogenation catalyst and hydrogen in considerable excess. Copper and/or cobalt catalysts can be used for the hydrogenation of glycerol. See U.S. Pat. No. 7,355,083 and WO 2007/099161.

R. Connor and H. Adkins, in J. Am. Chem. Soc. 54, 1932, pages 4678-4690, describe the hydrogenolysis of oxygen-containing organic compounds, such as glycerol, to 1,2-propanediol in the presence of a copper-chromium-barium oxide catalyst.

C. Montassier et al., in Bulletin de La Societe Chimique de France 1989, No. 2, pages 148-155, describe investigations into the reaction mechanism of the catalytic hydrogenation of polyols in the presence of various metallic catalysts, such as, for example, hydrogenation of glycerol in the presence of copper.

EP 0 523 015 describes a process for the catalytic hydrogenation of glycerol for the preparation of 1,2-propanediol and 1,2-ethanediol in the presence of a Cu/Zn catalyst at a temperature of at least 200° C. In this process, the glycerol is used as an aqueous solution having a glycerol content of from 20 to 60% by weight, the maximum glycerol content in the working examples being 40% by weight.

U.S. Pat. No. 5,616,817 describes a process for the preparation of 1,2-propane diol by catalytic hydrogenation of glycerol at elevated temperature and superatmospheric pressure, in which glycerol having a water content of not more than 20% by weight is reacted in the presence of a catalyst which comprises from 40 to 70% by weight of cobalt, if appropriate, manganese and/or molybdenum and a low copper content of from 10 to 20% by weight. The temperature is in the range of from about 180 to 270° C. and the pressure in a range of from 100 to 700 bar, preferably from 200 to 325 bar.

US 2008/0045749 discloses a two step process in manufacturing 1,2 propane diol from glycerol in which the glycerol is first subjected to a dehydrogenation reaction to produce a carbonyl compound, hydroxyacetone. The second step can comprise hydrogenating the acetone to 1,2-propane diol. It is mentioned that a promoted skeletal copper metal catalyst can be used in this second step. This process is complicated and specifically designed to accommodate manufacturing a second alternative compound from the acetone, in particular, manufacturing amino alcohol from an amine adduct of the acetone.

Other types of catalyst for hydrogenation of glycerol include acid resin catalysts (e.g, resins sold as Amberlyst® resins) in combination with hydrogenation catalysts, but there is need to find improved and more efficient catalysts for converting this increasingly abundant material into a useful product. Its use is more easily adopted when the product is relatively free of byproduct, e.g., 1,2-ethane diol, ("ethylene glycol" or "EG") and the process for manufacturing the 1,2 propane diol ("propylene glycol" or "PG") is more economical when the process is more selective for the desired diol and feedstock is not lost during the conversion. It would also be helpful if the processes for manufacturing the product involved less expensive processing conditions such as being operated in the liquid phase. There is the general problem, in delivering organic feed to a fixed bed reactor, of evenly distributing the feed radially across the reactor, i.e. across the diameter of the reactor bed. Vapor phase reactions, i.e., those in which the reactants are in the vapor phase, provides for even distribution, but using such phase reactors requires addition of equipment extraneous to the reactor, i.e., a vessel to heat and vaporize the glycerol and then sweep it into the reactor/catalyst bed with hydrogen. See U.S. Pat. No. 7,355,083. Such processes have been shown to achieve relatively good selectivity results for manufacturing 1,2 propane diol, but at a relatively higher cost. Vapor phase reactors not only require additional equipment, but also operate at relatively high temperatures, high ratio of hydrogen to feedstock, and lower throughput. Liquid phase reactions, on the other hand, pushes liquid through the reactor via a relatively inexpensive pump to move a thin film of liquid reactant(s) over the catalyst ("trickle bed" processes). These processes do not involve addition of equipment extraneous to the reactor. Liquid phase reactions have also been shown to evenly distribute reactant across catalyst, and at relatively good throughput. Good selectivity of 1,2 propane diol using such reactions however have not yet been seen.

SUMMARY OF THE INVENTION

This invention comprises a process for making 1,2-propane diol from glycerol. It has been discovered that subjecting a glycerol-containing feed stream to hydrogenation conditions in the presence of a transition metal promoted skeletal copper catalyst enhances selective production of the desired 1,2-propane diol product, with relatively minimal (less than 2% by weight) production of undesired by product such as 1,2-ethane diol. Chromium promoted catalyst is preferred for this invention, and moreover, it is preferred that the skeletal copper catalyst is prepared from copper-aluminum or copper-chromium-aluminum alloys that have been subjected to leaching conditions selected to lead to relatively high leaching of aluminum from the alloy, with preferably at least 40% of the aluminum in the starting alloy removed, and more preferably at least 50% of the starting aluminum removed. Catalysts prepared in such fashion generally have surface areas in the range of 5 to 50 m$^2$/g. These catalysts are particularly conducive to conducting the hydrogenation of glycerol added to the reactor in the liquid phase, e.g., at temperatures in the range of 180 to 210° C., and pressures in the range of 100 to 1000 pounds-per square inch gauge (psig). Such processes are preferred compared to those using vapor phase feeding systems, which can require additional equipment and/or energy usage. The catalysts used in this invention are particularly suitable for use in a fixed catalyst bed, but are also suitable for use in slurry based (stirred reactor) systems.

BRIEF DESCRIPTION OF THE DRAWINGS

FIG. 1 is plot of the weight percentages of metal shown in Table 1 for these examples. The selectivity illustrated is for 1,2 propane diol, and represents the mole percentage of the diol in the organic product produced by the inventive process. The illustrated conversion is the mole percentage of glycerol converted by the invention to organic product. The arrow in the figure points to selectivity and conversion for a catalyst that does not contain a transition metal.

FIG. 2 plots the selectivity and conversion versus a weight percentage Cr in Table 1 for each of these examples. The arrow in the figure points to selectivity and conversion for a catalyst that does not contain a transition metal.

DETAILED DESCRIPTION

Figure 1:
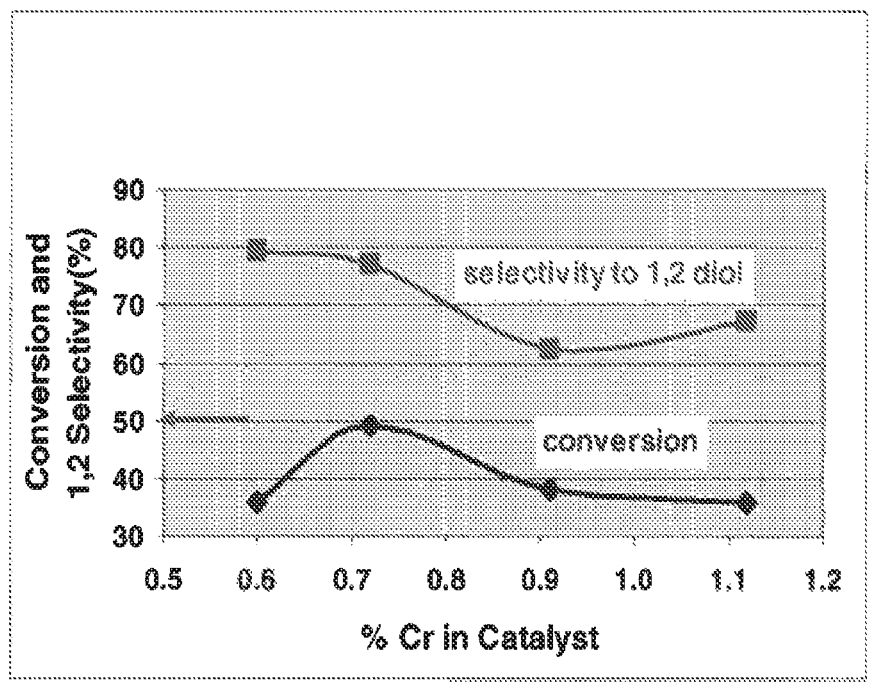
FIG. 1 is a graph illustrating conversion and selectivity of the invention using transition metal (Cr) promoted skeletal copper catalysts relative to the amount (weight %) of transition metal in the catalyst. The transition metal was added to the catalyst via a leachant solution pursuant to Examples 2-5.

The process of this invention is generally suitable for making 1,2-propane diol from any glycerol-containing stream. Suitable streams can include reagent grade glycerin, as well as glycerol by-product streams from industrial processes. These latter streams include glycerol-containing streams from the processing of oil- and/or fat-containing starting materials, for example from soap production, fatty acid and fatty acid ester production, etc. The glycerol-containing feed stream that is becoming more prevalent is that obtained in the preparation of alkyl esters of higher fatty acids by transesterification of fatty acid triglycerides, such as that obtained in the production of "biodiesel".

Glycerol-containing streams to be processed by this invention preferably have a water content of not more than 30% by weight, preferably not more than 20% by weight. A water content corresponding to glyceryl monohydrate (water content 16.3% by weight) or less is particularly suitable. The invention is also suitable for substantially anhydrous glycerol streams such as those described in US 2007/09916. A substantially anhydrous stream in this context includes streams having a water content of not more than 3% by weight, preferably of not more than 1% by weight.

The use of glycerol-containing streams having a water content in the range of up to 30% by weight, and in particular up to 20% by weight, permits the preparation of 1,2-propanediol in high yields and with high selectivity in the temperature and pressure range typically used for the hydrogenation. It is possible to use glycerol-containing streams containing higher amounts of water, and achieve relatively high yields and high selectivities for 1,2-propane diol, but, processing such streams is less economical because of reduced space-time yield due to dilution of the desired feedstream. Nevertheless, a water content in the general range of from 3 to 30% by weight is particularly suitable, with a range from 5 to 20% by weight, being especially suitable for maintaining a suitable viscosity for the glycerol stream during the hydrogenation.

While not preferable, the glycerol-containing streams may include glycerol-miscible organic solvent instead of or in addition to water. Such glycerol-containing streams would preferably have a total solvent content of no more than 20% by weight, particularly preferably no more than 10% by weight of the stream. If solvent is used in addition to water, the solvent in the solvent/water mixture is preferably not more than 50% by weight, particularly preferably not more than 20% by weight, based on the total weight of the solvent/water mixture. Suitable glycerol-miscible organic solvents are $C_1$ to $C_4$-alkanols, such as methanol, ethanol, n-propanol, isopropanol, n-butanol, tert-butanol, polyols and mono- and dialkyl ethers thereof, cyclic ethers, such as dioxane and tetrahydrofuran, etc. Other suitable solvents are aromatic hydrocarbons, such as benzene, toluene or the xylenes.

The glycerol-containing streams may be subjected to conditioning processes prior to hydrogenation, including purification processes to remove undesired components and/or water and organic solvent. Glycerol-containing feedstreams, for example, may comprise inorganic salts and catalyst poisons, i.e. components which adversely affect (e.g., deactivate) the hydrogenation catalyst, and/or which adversely affect processes conducted on the diol product of this invention downstream, e.g., distillation to purify the 1,2-propane diol product. Catalyst poisons include, for example, nitrogen-containing compounds, such as amines, and sulfur-containing compounds, such as sulfuric acid, hydrogen-sulfide, thioalcohols, thioethers, e.g., dimethyl sulfide, carbon oxide sulfide, amino acids, e.g. amino acids comprising sulfur and additional nitrogen groups, fatty acids and salts thereof. The catalyst poisons may further include halogen compounds, traces of conventional extracting agents, e.g. acetonitrile or N-methylpyrrolidone, etc. and, if appropriate, organic phosphorus and arsenic compounds. A catalyst poison frequently present in glycerol-containing streams from oil and fat refining is sulfuric acid, which is used as a catalyst in an esterification step upstream. Similarly sodium hydroxide, potassium hydroxide or other sodium or potassium salts such as carbonates and sulfates may be present due to upstream transesterification processes. Processes to remove these contaminants are well known, and include thermal treatments, distillation, adsorption, ion exchange, membrane separation, or a combination of two or more of these methods. Membrane separation methods employ membranes having selective pore sizes for reducing the water content and/or salt removal.

Adsorbents chosen to treat the glycerol-containing streams to remove components which adversely affect the catalytic hydrogenation generally have a specific surface area, determined according to BET, in the range of from about 10 to 2000 $m^2/g$, preferably in the range of from 10 to 1500 $m^2/g$, more preferably in the range of from 10 to 400 $m^2/g$, especially in the range of from 60 to 250 $m^2/g$. Suitable adsorbents are, for example, activated aluminas, e.g., those that are prepared from aluminum hydroxide, which is obtainable from aluminum salt solutions by conventional precipitation methods. Active aluminas suitable for the process according to the invention are also obtainable starting from aluminum hydroxide gels. Suitable adsorbents also include alumina-containing solids, which include clay. Other suitable adsorbents are aluminum phosphates, silica, titania, zirconia, and activated carbon.

The glycerol-containing stream may also be subjected to a catalytic desulfurization, if appropriate in the presence of hydrogen, for reducing the contents of sulfur-containing compounds, especially sulfur-containing aromatic compounds. Suitable desulfurization agents are described in US Patent Application 2007/099161, the contents of which are incorporated by reference.

The configuration of process equipment for carrying out one or more of the aforementioned conditioning processes is well within the skill of those skilled in the art. It is also well known how one would configure these processes in connection with a hydrogenation reaction.

The glycerol-containing streams according to the invention preferably originate from the production of fatty acid monoalkyl esters that are obtained from biogenic oil- and/or fat-containing starting mixtures and can be used as fuel in diesel engines. US Patent Application 2007/099161, the contents of which are incorporated herein by reference, describes suitable types of biogenic materials from which glycerol may originate.

Preferably, the glycerol-containing stream is produced in the following general process: (1) providing a biogenic fat- and/or oil-containing starting mixture, (2) transesterification of the fatty acid triglycerides present in the starting mixture with at least one monoalcohol and, if appropriate, esterification of the free fatty acids present in the starting mixture with formation of an esterification mixture, (3) separation of the esterification mixture to obtain at least one fraction enriched with biodiesel and at least one fraction enriched with glycerol liberated in the esterification, and (4) if appropriate, conditioning the fraction enriched with glycerol. These processes are well known in the art. See US Patent Application 2007/099161.

The glycerol-containing stream of this invention is preferably added to the reactor in the liquid phase.

The hydrogenation is carried out using skeletal copper catalysts. The term "skeletal copper catalysts", as used herein and in the appended claims, means a porous catalytic alloy based material comprising copper and aluminum. The alloy may further contain small amounts of other metals such as Cr and the like. These metals are added as a promoter as described below. These porous materials, when microscopically viewed, take on a skeletal, sometimes referred to as a "sponge-like", appearance having tortuous pore channels throughout the particle. These high surface area products have been found to have sites for hydrogen activation and, thus, exhibit catalytic hydrogenation activity.

The porous catalyst is formed by using conventional metallurgical techniques to first form a precursor alloy of copper and aluminum (optionally having small amounts of up to about 10 weight percent of the aforementioned promoter metals, therein) in which the copper is present in from about 35 to 60 weight percent, with the remainder being primarily aluminum. The formed alloy is crushed and/or ground and classified by passing it through a sieve to provide a material having a desired size. Larger particles exiting the grinding mechanism can be recycled for further grinding.

The formed alloy is then subjected to an aqueous alkali (e.g., sodium hydroxide) solution to extract the aluminum metal from the alloy. When granular, fixed bed type (cross sectional diameter of about 1 to 8 mm) catalyst is desired, the aluminum is partially extracted ("leached"), to the extent of leaching 20%-80%, preferably 40-60%, and more preferably at least 50% of the aluminum (Al) originally present, to obtain a final catalyst composition with about 10 to 60, preferably 20 to 55 weight percent Al and the balance as copper and promoters if present. The skeletal copper catalyst can be formed according to the process described in U.S. Pat. Nos. 1,628,190; 1,915,473; 2,139,602; 2,461,396; and 2,977,327. The teachings of these patents are incorporated herein in their entirety by reference.

Catalysts designed for a slurry reactor are prepared using the above techniques, except that the particles are ground to be less than 500 microns, more typically less than 75 microns, and frequently, in the range of 10 to 50 microns. The leaching conditions described above also are chosen to leave a catalyst having lower aluminum amounts, e.g., 1 to 10% aluminum, and more desirably 2 to 5% by weight aluminum.

Skeletal copper catalysts made in the above manner are well known, and are part of a family of metal alloy derived products sold by W. R. Grace & Co.-Conn. under the trademark "RANEY®."

The alkali solution used to leach out the aluminum metal present is from either an inorganic (preferred) or organic compound. Conventional processes utilize an aqueous solution having from about 2 to 35 weight percent concentration of an alkali metal hydroxide (e.g., sodium hydroxide) employed as the leaching agent, preferably 5 to 10% by weight for a fixed bed catalyst, or preferably 20-30% for a slurry catalyst, from which a much larger fraction of aluminum is extracted. The alloy is usually treated at elevated temperatures of from about 30° C. to 110° C., preferably 30 to 60° C. for fixed bed catalysts and 60 to 100° C. for slurry catalysts. Alloy particles being processed for fixed bed catalysts sit in a vessel through which the alkali is pumped and/or re-circulated. For alloys processed for slurry activation, the alkali solution is stirred and the alloy powder can be directly added to the alkali solution, or it can be formed into an aqueous suspension, which is then contacted with the alkali solution. The aluminum contained in the alloy dissolves to form an alkali metal aluminate (e.g., sodium aluminate) with vigorous evolution of hydrogen. If silicon is also present in the alloy, the base forms the corresponding alkali metal silicate. The powder and alkali are normally allowed to remain in contact with each other for several hours at elevated temperature (e.g., 40°-60° C.) until the aluminum (or silicon) content is reduced to the desired level. Indeed, it has been determined for this invention that the fixed bed skeletal metal copper catalyst can be advantageously prepared using relatively high or "aggressive" leaching conditions in terms of temperature and residence time in the leaching bath. Preferred leaching conditions include those that can remove at least 40% or more of the aluminum originally present in a reasonably short batch time, e.g. greater than 8% NaOH solution applied at greater than 40° C. for 90 minutes or more. The Examples below indicate that more extensive leaching leads to a porosity that has a higher sustainable rate of conversion of glycerol when the catalyst is used in a fixed bed process. The term "fixed bed", as used herein, refers to a mass of catalyst which is packed in a constrained static bed within a catalytic reactor, and through which the reactant mixture moves continuously, as opposed to a stirred or fluidized bed ("slurry" system) which moves constantly within a reactor, along with the reactant mixture.

The skeletal metal catalyst after activation is separated from the reaction liquor and then conventionally washed with water until the wash water has a slightly alkaline pH value of about 8 to 9. The pore volume, pore size and surface area of the catalyst will depend upon the amount of aluminum (or silicon) in the initial alloy and the degree of leaching.

The skeletal copper catalyst is promoted with at least 0.5 and up to 15% by weight of a promoter transition metal, depending on the specific promoter metal. Such transition metals include those capable of promoting the hydrogenation performance of the copper catalyst, e.g., selectivity, conversion rate and stability against deactivation. The skeletal copper catalyst of this invention preferably has a promoter transition metal content in the range of about 0.5 to 10%. Such metals include, but are not limited to, transition metals (other than copper) in Group IIB, IVB, VIIB, VIIB, VIIIB of the Periodic Chart, and combinations thereof. Specific metals include, but are not limited to, chromium, palladium, platinum, ruthenium, molybdenum, rhenium, manganese, nickel, zinc, zirconium, tungsten and combinations of two or more of the same.

Chromium is a preferred transition metal promoter, and is preferably included such that chromium comprises 0.5 to 5% by weight of the skeletal copper catalyst.

The promoter transition metals are typically added to the catalyst as a component in the base alloy of copper and aluminum as mentioned above, but could also be added in the leaching solution used to remove aluminum from copper aluminum alloy, or in an impregnation or coating bath following activation. If added via the leaching solution, one can include therein, an amount of promoter precursor, e.g., chromium chloride or other Cr compound equivalent, to a metal:catalyst ratio of about 0.2 to 2% by weight, preferably 0.5 to 1.5% by weight.

When using the option of applying promoters to the surface of the catalyst after activation, surface deposition is conducted during a post-activation washing stage wherein the catalyst is contacted with a (usually alkaline-pH) salt solution, to achieve the same approximate ranges of promoter described above. This surface deposition can be done at a chosen pH in e.g. the range of 9-12 preferably 10-11. The catalyst is stored under water at an alkaline pH of usually 9-11. In another post leaching process, the metal can be plated onto the catalyst utilizing coating or plating techniques described in the U.S. Pat. No. 7,375,053, the contents of which are incorporated herein by reference.

The above catalysts are more efficiently utilized in continuous processes, including those using a fixed catalyst bed. A trickle-bed procedure can be used with a fixed catalyst bed. The catalysts utilized in conventional fixed bed processes can be in various forms, including, but not limited to, pressed cylinders, tablets, lozenges, wagon wheels, rings, stars, or extrudates, such as solid extrudates, polylobal extrudates, hollow extrudates and honeycomb bodies.

The above catalysts can also be utilized in other processes such as those using a continuous slurry tank reactor, or batch wise slurry processes. The term "slurry process" is used to embrace both of the non-fixed bed processes. The catalysts in slurry processes are usually finely divided particulate having an average particle size mentioned above. Catalyst is generally added to the slurry reactor at a weight ratio of catalyst to reactant in the range of 1:30 to 1:4.

Excess hydrogen is preferably circulated in the hydrogenation process, it being possible for a small part to be discharged as waste gas for removing gaseous by product materials. The molar ratio of hydrogen to glycerol is preferably from 2:1 to 500:1, preferably from 3:1 to 100:1, and most preferably 10:1 to 50:1, which equates to about 2000-10,000 volume ratio.

It is possible to use one reactor or a plurality of reactors which can be connected in series or parallel to one another.

The temperature for the process of this invention is generally from 180 to 210° C., and frequently from 190 to 200° C. The temperature is preferably selected to maintain a liquid to partially liquid mixture within the reactor, while the reactant mixture coming into the reactor is preferably a continuous liquid phase, which may be pumped into the reactor under pressure. The reaction pressure is preferably from 7 bar to 20 bar (100 psig to 300 psig).

The space velocity in a continuous process embodiment of the invention is preferably from 0.05 to 0.30, more preferably from 0.10 to 0.20 kg of glycerol to be hydrogenated per kg (catalyst) per h. The conversion of glycerol to product, based on glycerol, is preferably at least 50%, and in particular at least 60% in a continuous fixed bed process, although catalysts of this invention processed for slurry reactors have lower conversion rates. Since the process of this invention has relatively low level selectivity for by products such as ethylene glycol, unconverted glycerol can be easily recycled for further processing as described below.

The process of this invention produces an organic product substantially comprising 1,2-propanediol. Indeed, in one embodiment, a fixed bed process using a promoted skeletal copper catalyst exhibits relatively high selectivity for 1,2-propane diol. The selectivity of the invention for the product, based on 1,2-propanediol, is typically at least 70%, more often and preferably at least 80% by weight of the organic product. Higher selectivities of up to 90% or more can be achieved. Selectivities, however, vary depending on feedstock, temperature and/or pressure in the hydrogenation, and type of hydrogenation, e.g., slurry versus fixed bed reactor. Further constituents in the organic products of these processes can include, albeit preferably in relatively little amounts, methanol, ethanol, n-propanol, isopropanol, 1,3-propanediol, 1,2-ethane diol (ethylene glycol), acrolein, lactic acid, and water. It is desirable if the organic product of the process comprises less than 2% by weight ethylene glycol.

Because the process of the invention is selective, any unconverted glycerol remaining in the product should have little impurity, and can be recycled to the hydrogenation stage, with relatively little processing. Accordingly, any glycerol recovered from the process may be subjected to further conditioning, including adsorption and other purification steps designed to remove impurities, e.g, catalyst fines, reactant impurities, and the like, that could affect the application in which the glycerol will be utilized.

To further illustrate the present invention and the advantages thereof, the following specific examples are given. The examples are given as specific illustrations of the claimed invention. It should be understood, however, that the invention is not limited to the specific details set forth in the examples.

All parts and percentages in the examples, as well as the remainder of the specification, which refers to solid compositions or concentrations, are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

Slurry Reactor Catalyst

Example 1

A precursor alloy was made by conventional melting and mixing techniques at a composition of 50% Cu-50% Al. The cooled alloy was crushed and ground to a powder with average particle size of 15 microns. The alloy was converted to a catalyst by gradual addition, with stirring, to a leachant solution comprising 23% aqueous NaOH, the addition being controlled to achieve a temperature not exceeding 80° C. The mixture of leachant and alloy was stirred for an additional 1 hour while maintaining 80° C. After this activation period the stirring of the mixture was discontinued to allow settling of catalyst particles and the removal of excess byproduct solution (NaOH and sodium aluminate) from the settled catalyst. The catalyst was then washed with water (by cycles of water addition, stirring, settling and spent solution removal) until the pH of the aqueous phase reached 9.

The finished catalyst product had an average particles size of 14 microns (via Malvern analysis) and a chemical composition of 1.2% Al and 97.9% Cu.

Example 2

A catalyst using the alloy and activation as described in Example 1 was prepared, with the modification of adding 3.16 g $CrCl_3$ to the leachant solution for 300 g of alloy to be activated, and stirring the NaOH solution and $CrCl_3$ to ensure dissolution of the Cr species before use.

The finished catalyst product had an average particles size of 38 microns (via Malvern analysis) and a chemical composition of 0.6% Cr, 1.4% Al, and 97.7% Cu.

Example 3

A catalyst using the alloy and activation as described in Example 1 was prepared, with the modification of adding 4.43 g $CrCl_3$ to the leachant solution for 350 g of alloy to be activated, and stirring the NaOH solution and $CrCl_3$ to ensure dissolution of the Cr species before use.

The finished catalyst product had an average particles size of 36 microns (via Malvern analysis) and a chemical composition of 0.7% Cr, 1.6% Al and 97.3% Cu.

Example 4

A catalyst using the alloy and activation as described in Example 1 was prepared, with the modification of adding 5.54 g $CrCl_3$ to the leachant solution for 350 g of alloy to be activated, and stirring the NaOH solution and $CrCl_3$ to ensure dissolution of the Cr species before use.

The finished catalyst product had an average particles size of 35 microns (via Malvern analysis) and a chemical composition of 0.9% Cr, 1.8% Al and 96.9% Cu.

Example 5

A catalyst using the alloy and activation as described in Example 1 was prepared, with the modification of adding 6.65 g $CrCl_3$ to the leachant solution for 350 g of alloy to be activated, and stirring the NaOH solution and $CrCl_3$ to ensure dissolution of the Cr species before use.

The finished catalyst product had an average particle size of 30 microns (via Malvern analysis) and a chemical composition of 1.1% Cr, 1.9% Al and 96.6% Cu.

Example 6

A catalyst using the alloy and activation as described in Example 1 was prepared, with the modification of adding 1.7% Cr metal to the alloy mixture in place of 1.7% of the Cu (i.e. retaining 50% Al).

The finished catalyst product had an average particle size of 32 microns (via Malvern analysis) and a chemical composition of 3.2% Cr, 6% Al and 90.1% Cu.

Example 7

A catalyst using the alloy and activation as described in Example 1 was prepared, with the modification of adding 1.3% Cr metal to the alloy mixture in place of 1.7% of the Cu (i.e. retaining 50% Al).

The finished catalyst product had an average particle size of 43 microns (via Malvern analysis) and a chemical composition of 2.4% Cr, 3.9% Al and 91.9% Cu.

Example 8

A catalyst using the alloy and activation as described in Example 1 was prepared, with the modification of adding 0.8% Cr metal to the alloy mixture in place of 1.7% of the Cu (i.e. retaining 50% Al).

The finished catalyst product had an average particle size of 21 microns (via Malvern analysis) and a chemical composition of 1.5% Cr, 4.9% Al and 92.2% Cu.

Example 9

A catalyst using the alloy and activation as described in Example 1 was prepared, with the modification of adding 0.6% Cr metal to the alloy mixture in place of 1.7% of the Cu (i.e. retaining 50% Al).

The finished catalyst product had an average particle size of 48 microns (via Malvern analysis) and a chemical composition of 1.0% Cr, 9.6% Al and 88.0% Cu.

Each of the catalysts prepared in accordance with Examples 1-9 are then tested in a slurry reactor. Specifically, catalytic testing is performed in a stirred autoclave charged with 500 g of an 80% glycerin 20% water solution and 20% by weight of the tested catalyst based on the glycerin wt. The reaction was carried out 16 hours for each catalyst at 190° C., 200 psig, while stirring the reactant and catalyst at 1600 rpm. The reaction mixture is sampled every 2 hrs during the reaction and this sample is analyzed by a HP 5890 GC gas chromatography instrument (FID detector and an electronic integration) (GC) using conventional GC methods as follows:

Example 10

A catalyst was prepared using the alloy (200 g quantity) and activation as described in Example 1. The activated catalyst was washed to pH 11 and then treated by addition of 3 g of $KMnO_4$ dissolved in 200 ml of water. After stirring the catalyst-permanganate mixture for 30 minutes the catalyst was washed with water to pH 9.

The finished catalyst product had an average particle size of 21 microns (via Malvern analysis) and a chemical composition of 1.2% Mn, 0.8% Al and 98.5% Cu.

Capillary column: 60 m, 0.53 mm internal diameter and film thickness of 1 micrometer.
Instrument Conditions:
Split vent: 50 ml/min
Air flow: 300 ml/min
Hydrogen flow: 30 ml/min
Head pressure: 15 psi
Signal range: 7
Injection volume: 0.5 microliters
Temperature program: Initial temperature 35° C., hold 4 minutes, ramp 15° C./min to 185° C., hold 10 min.
Injection and detector temp: 220° C. and 260° C.
Take from sample solution 25 microliters, dissolve in 900 microliters water and 500 microliters IS solution. The IS solution is 1,4-Butanediol in Dioxane (10 mg/ml).

The analyzed compounds include primarily the desired product 1,2 propanediol ('propylene glycol' or 'PG'), unconverted glycerine, and byproducts ethylene glycol ('EG'), 1,3 propanediol ('1,3'), and ethanol. The final reaction product mixture is also weighed and the apparent weight (wt.) loss from this is calculated and compared to that from the unaccounted-for mass based on GC analysis (after summing analyzed concentrations). The weight loss is assumed to be via $CO_2$ gas and is a sign of over-reaction which is irreversible under reasonable conditions and therefore is to be minimized. Finally the ratio of % conversions at 16 vs. 8 hours (hr) is used as a sign of 'stability' of the catalyst. A number of 2 or higher being desirable and a significantly lower number indicating serious catalyst deactivation. The data for each of the above measurements and/or calculations is provided in Table 1 below for each catalyst sample. The results for each catalyst represent the final (16 hr) sample taken during the reaction, except for the stability ratio which is based on the 16 hr vs. 8 hr sample.

TABLE 1

| Example No. | Addition Point for Cr * | Wt % Cr in Catalyst | % Conversion | PG Selectivity | EG Selectivity | 1,3 Selectivity | % Yield | % Wt lost | % ID (GC) | Stability |
|---|---|---|---|---|---|---|---|---|---|---|
| 1 | None | 0 | 49 | 48 | 4 | 0.6 | 24 | 8 | 82 | 1.41 |
| 2 | Leachant | 0.6 | 36 | 79 | 2 | 0 | 28 | 5 | 89 | 1.24 |
| 3 | Leachant | 0.7 | 49 | 77 | 3 | 0 | 38 | 6 | 92 | 1.44 |
| 4 | Leachant | 0.9 | 38 | 63 | 2 | 0 | 24 | 3 | 89 | 1.20 |
| 5 | Leachant | 1.1 | 36 | 67 | 3 | 0 | 24 | 6 | 91 | 1.41 |

TABLE 1-continued

| Example No. | Addition Point for Cr * | Wt % Cr in Catalyst | % Conversion | PG Selectivity | EG Selectivity | 1,3 Selectivity | % Yield | % Wt lost | % ID (GC) | Stability |
|---|---|---|---|---|---|---|---|---|---|---|
| 6 | Alloy (1.7) | 2.8 | 16 | 95 | 2 | 0 | 15 | 4 | 100 | 1.45 |
| 7 | Alloy (1.3) | 2.4 | 21 | 91 | 3 | 0.4 | 19 | 4 | 100 | 2.55 |
| 8 | Alloy (0.83) | 1.48 | 27 | 79 | 3 | 0.7 | 21 | 3 | 99 | 1.87 |
| 9 | Alloy (0.57) | 0.95 | 33 | 55 | 2 | 0.1 | 18 | 5 | 88 | 1.58 |
| 10 | MnCu | | 39 | 58 | 3 | 0 | 22 | 2 | 89 | 1.27 |

* For examples 6-9, the number in parentheses reflects the amount of Cr in the alloy used to make the final catalyst.

Figure 2:
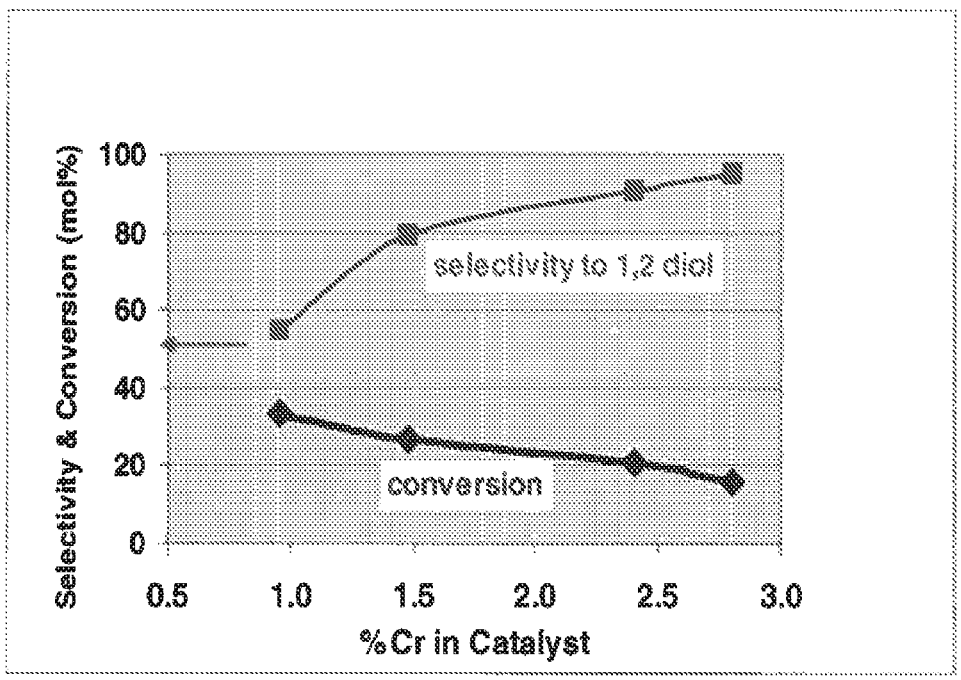
FIG. 2 is a graph illustrating conversion and selectivity of another embodiment of the invention using transition metal (Cr) promoted skeletal copper catalysts. As with FIG. 1, the conversion and selectivity (each in mole %) is shown relative to the amount (weight %) of transition metal in the catalyst. The transition metal of this embodiment, however, was added to the catalyst as component of the alloy used to make the skeletal copper catalyst, as made pursuant to Examples 6-9.

From the above, it can be concluded, that:
1. Promotion of the catalyst, e.g., by chromium, enhances selectivity of skeletal metal copper catalyst for 1,2-propane diol, albeit, at lower conversions. See especially Examples 6 and 7 compared to Example 1. Unpromoted catalyst did show lower amounts of some undesired by products such as ethylene glycol.
2. Promotion of catalyst through addition of promoter in an alloy performs better in terms of selectivity compared to adding the promoter in leachant. The degree of selectivity seen by the former would not be expected from the trend of results shown for the latter. See FIG. 1 (alloy) and FIG. 2 (leachant).
3. The invention is achieving relatively good selectivities in liquid phase reactions and is relatively equivalent in terms of selectivity shown for vapor phase reactions such as that described in U.S. Pat. No. 7,355,083.

Fixed Bed Catalysts

Example 11

The unpromoted Cu—Al alloy of Example 1 was crushed and sieved to particulate having a size in the range of 2 to 3 millimeters [8-12 mesh range]. This alloy was placed in a vessel for leaching, through which 10% NaOH solution was circulated at 38° C. for 30 minutes. The catalyst was then washed to a pH of 8.35.
The final composition of the catalyst was 58% Cu and 42% Al which equates to leaching (removal) of 28% of the original aluminum in the alloy.

Example 12

The alloy and leaching method of Example 11 were applied except that the temperature in activation (leaching) was 45° C. and the time was 60 minutes.
The final composition of the catalyst was 62% Cu and 38% Al which equates to leaching (removal) of 38% of the original aluminum in the alloy.

Example 13

The alloy and leaching method of Example 11 were applied except that the temperature in activation (leaching) was 45° C. and the time was 90 minutes.
The final composition of the catalyst was 68% Cu and 32% Al which equates to leaching (removal) of 53% of the original aluminum in the alloy.

Example 14 [Comparative]

The catalyst sample, (Cu-1808 T ⅛, Product code 05804910250, Lot No: 80) was obtained from Engelhard, Elyria, Ohio. It was sent as ⅛" extrudates which were crushed and sieved to 10-20 mesh prior use. Fourteen cc of the same were charged in the reactor using column vibrator to ensure uniform packing of the catalyst bed. The catalyst was pre-hydrogenated in situ by following activation protocol. The reactor was purged with inert at 50 cc/min for 30 minutes then the flow was switched to 150 cc/min hydrogen. The temperature of the bed was raised to 190° C. over 30 minutes and held at that setting for 2 hours. The catalyst was cooled to ambient temperature and kept in hydrogen until use. Subsequently the fixed bed testing protocol was as described below.

Example 15

The Cr-promoted alloy and leaching method of Example 11 were applied except that the temperature in activation (leaching) was 45° C. and the time was 90 minutes.
The final composition of the catalyst was 3.3% Cr, 72% Cu and 24% Al which equates to leaching (removal) of 68% of the original aluminum in the alloy.

Example 16

The Cr-promoted alloy of Example 11 and leaching method of Example 13 were applied except for a time of 70 minutes (at 45° C.).
The final composition of the catalyst was 1.8% Cr, 67% Cu and 30% Al which equates to leaching (removal) of 56% of the original aluminum in the alloy.

Example 17

The Cr-promoted alloy of Example 11 and leaching method of Example 15 were applied.
The final composition of the catalyst was 1.1% Cr, 68% Cu and 30% Al which equates to leaching (removal) of 57% of the original aluminum in the alloy.

Example 18

The Cr-promoted alloy of Example 11 and leaching method of Example 15 were applied.
The final composition of the catalyst was 0.7% Cr, 66% Cu and 33% Al which equates to leaching (removal) of 50% of the original aluminum in the alloy.

Example 19

A Cr-promoted catalyst was prepared using the unpromoted alloy of Example 11 combined with leaching by the method of Examples 2-5, i.e., with 2.0 g ammonium chromate added to the leachant solution per 100 g of alloy. The activation time and temperature were 60 minutes and 45° C., respectively.

The final composition of the catalyst was 0.5% Cr, 68% Cu and 30% Al which equates to leaching (removal) of 46% of the original aluminum in the alloy.

Each of the catalysts prepared in accordance with Examples 10-19 is then placed in a fixed bed reactor (a ½ inch inner diameter tube) while still immersed in water. Any free space in catalyst-charged reactor is purged of air using inert gas flow, then the reaction is run by flowing hydrogen and glycerine feed solution over the catalyst. The catalyst size range is 8-12 mesh or approximately 2-3 mm diameter. The catalyst shape is granular as achieved by the crushing/sieving process described earlier.

Before entering the reactor, the glycerin and the hydrogen flow pass through a preheating box kept at 140° C. The reactor Catalyst performance is then ranked based on % conversion of glycerin (GL) (normalized to residence time in contact with the catalyst bed), % selectivity to the desired 1,2 propanediol ('propylene glycol' or 'PG'). The % of aluminum (Al) leached in weight percent is provided in the table, which is calculated as indicated in Table 2 below.

Catalyst performance in terms of the above the above selectivities is measured at various stages in the reaction measured in terms of the reaction time, i.e., Stage 1 is measured in a period extending from 48 hours from initiating the reaction to 72 hours, Stage 2 is defined as 72-120 hours, and Stage 3 is defined as 120-168 hours. GC measurements are taken every 8 hours during the Stage reflected and then averaged and reported below for the relevant stage.

Catalyst Stability is calculated for each catalyst based on conversion of GL. One measurement is a ratio of the conversion at Stage 3 and that at Stage 1, and the second number is the ratio of the conversion at Stage 3 and that at Stage 2.

TABLE 2

| Example No. | Description | % Al Leached* | Addition Point for Cr | Cr (%, cat) | Conversion GL % | | | Selectivity 12PG % | | | Yield 12PG, % | | | Stability | |
|---|---|---|---|---|---|---|---|---|---|---|---|---|---|---|---|
| | | | | | Stage 1 48-72 h | Stage 2 72-120 h | Stage 3 120-168 h | Stage 1 48-72 h | Stage 2 72-120 h | Stage 3 120-168 h | Stage 1 48-72 h | Stage 2 72-120 h | Stage 3 120-168 h | Conv Stage 3/1** | Conv 3/2 |
| 11 | Unpromoted Cu, low leach | 28 | NA | 0 | 70 | 54 | — | 68 | 92 | — | 47 | 49 | — | 0.77 | |
| 12 | Unpromoted Cu, med leach | 38 | NA | 0 | 80 | 70 | 66 | 67 | 71 | 66 | 54 | 49 | 43 | 0.83 | 0.94 |
| 13 | Unpromoted Cu, high leach | 53 | NA | 0 | 74 | 72 | 73 | 72 | 89 | 93 | 53 | 64 | 68 | 0.99 | 1.01 |
| 14 (comparative) | CuCrOx | NA | co-precipitated | NA | 36 | 33 | — | 85 | 93 | — | 29 | 31 | — | 0.92 | |
| 15 | 1.7% Cr alloy, high leach | 68 | alloy | 3.2 | 79 | 79 | 79 | 80 | 81 | 83 | 64 | 64 | 66 | 1.00 | 1.00 |
| 16 | 1.2% Cr alloy, high leach | 56 | alloy | 1.8 | 68 | 75 | 70 | 76 | 74 | 75 | 52 | 55 | 52 | 1.03 | 0.93 |
| 17 | 0.75% Cr alloy, high leach | 57 | alloy | 1.1 | 84 | 86 | 89 | 70 | 71 | 71 | 58 | 61 | 63 | 1.06 | 1.04 |
| 18 | 0.50% Cr alloy, high leach | 50 | alloy | 0.7 | 65 | 68 | 67 | 68 | 64 | 70 | 45 | 44 | 46 | 1.02 | 0.98 |
| 19 | Low Cr in leachant, medium leach | 46 | leachant | 0.5 | 67 | 64 | 58 | 66 | 66 | 56 | 44 | 42 | 33 | 0.87 | 0.91 |

*Calculated as 100*[% Al(cat)/% Ni(cat)]/[% Al(alloy)/% Ni(alloy)]
**The data for Example 11 is a ratio of Stage 2 and Stage 1. Conversion was not taken for Stage 3, because the catalyst showed significantly decreased conversion after Stage 2, and was estimated it would have had less than 50% by Stage 3.

contains a back pressure regulator (BPR) at the exit line of the reactor which is set to the desired process pressure. The two flows enter the top of the reactor and after efficient mixing through the fitted filters in the pre-heating zone trickle down the catalyst bed. The conditions in the reactor are as follows: 200 psig, 190° C., glycerol-containing feed of 20 wt % water/80 wt % glycerol, 14 ml catalyst bed volume, and 0.05 cc/min liquid feed flow rate.

The reactant flow exits the reactor and enters the BPR to step down the pressure to ambient. After the BPR, the two gas-liquid flows pass through a condenser kept at 25° C. The exit flow is either switched to the waste flask during stabilization step or to the collection flask during routine reaction step. The gas phase is next passed through a liquid trap held at −36° C. to quenched low boiling products carried with the hydrogen flow. The weight and the volume of the reaction solution collected over given period of time is measured accurately and analyzed by GC for product distribution.

Figure 3:
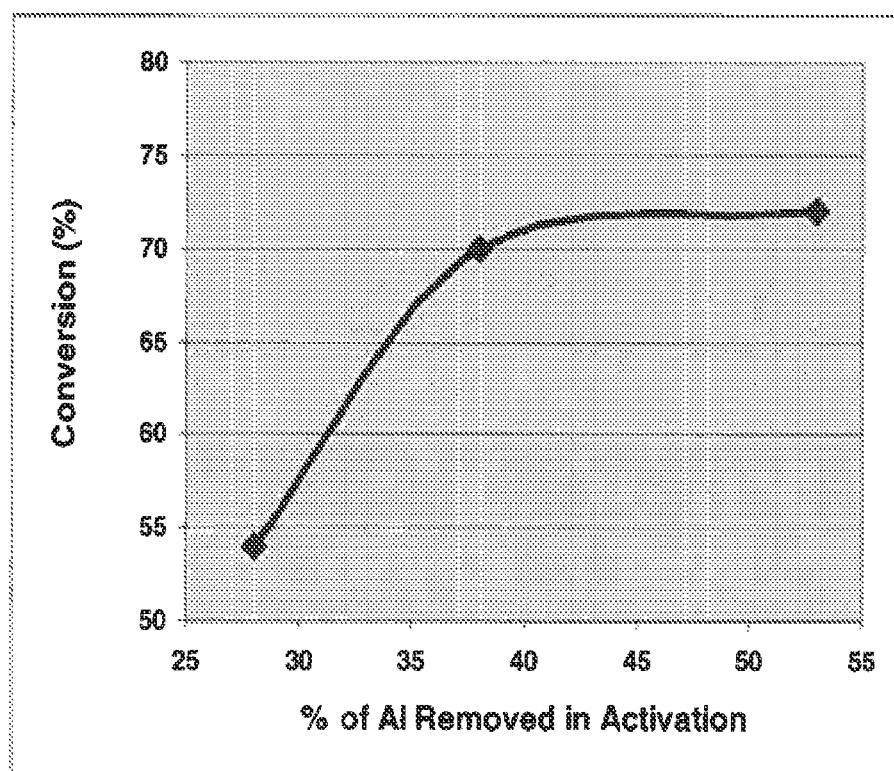
FIG. 3 is a graph illustrating conversion of glycerol to organic product when using the invention relative to the amount of aluminum leached from alloy typically used in making the type of catalyst used in the invention. The data plotted in this figure is that shown for Stage 2 conversion data for Examples 11-13 in Table 2 and represents a stabilized time period during which conversion is neither increasing or decreasing.
Figure 4:
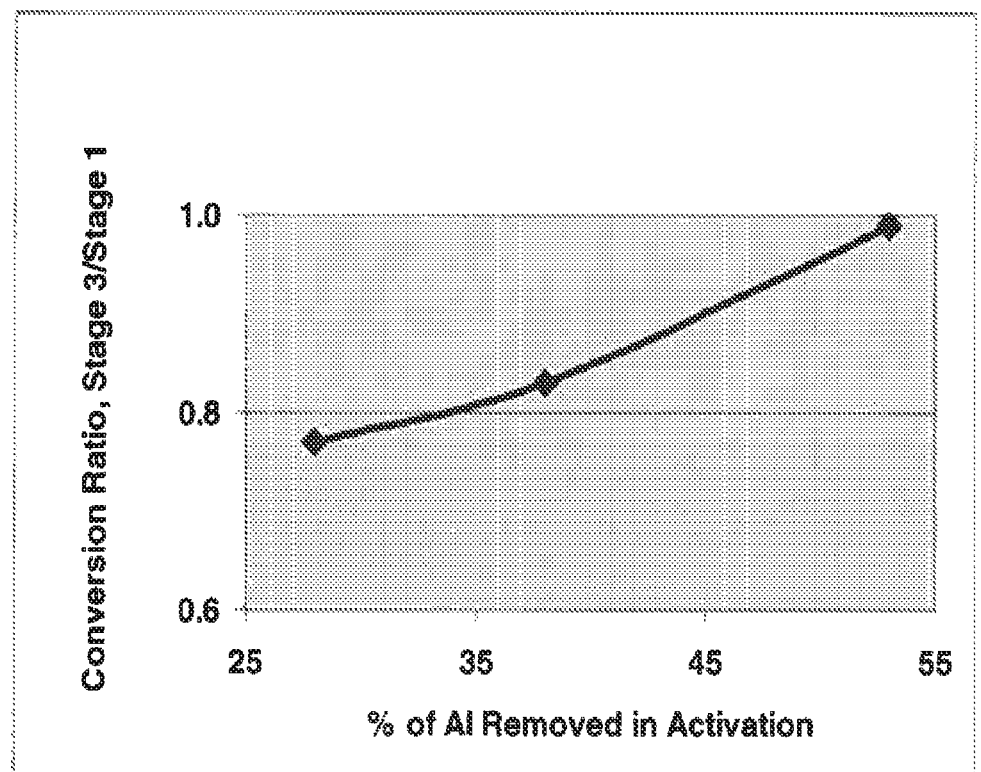
FIG. 4 is a graph illustrating conversion of glycerol to organic product when using the invention relative to the amount of aluminum leached from the alloy typically used in making the type of catalyst used in the invention. The conversion data plotted in this figure is a ratio used to illustrate the stability of the invention's conversion rate over time. The plotted data comes from conversion data for Examples 11-13 in Table 2, and is a ratio of conversion after Stage 3 (except for Example 11 as noted in Table 2) divided by conversion rates achieved after Stage 1.

From the above, it can be concluded, that:

(1) Higher extent of aluminum removed enhances % conversion and catalyst stability. See FIG. 3 and FIG. 4.

Figure 5:
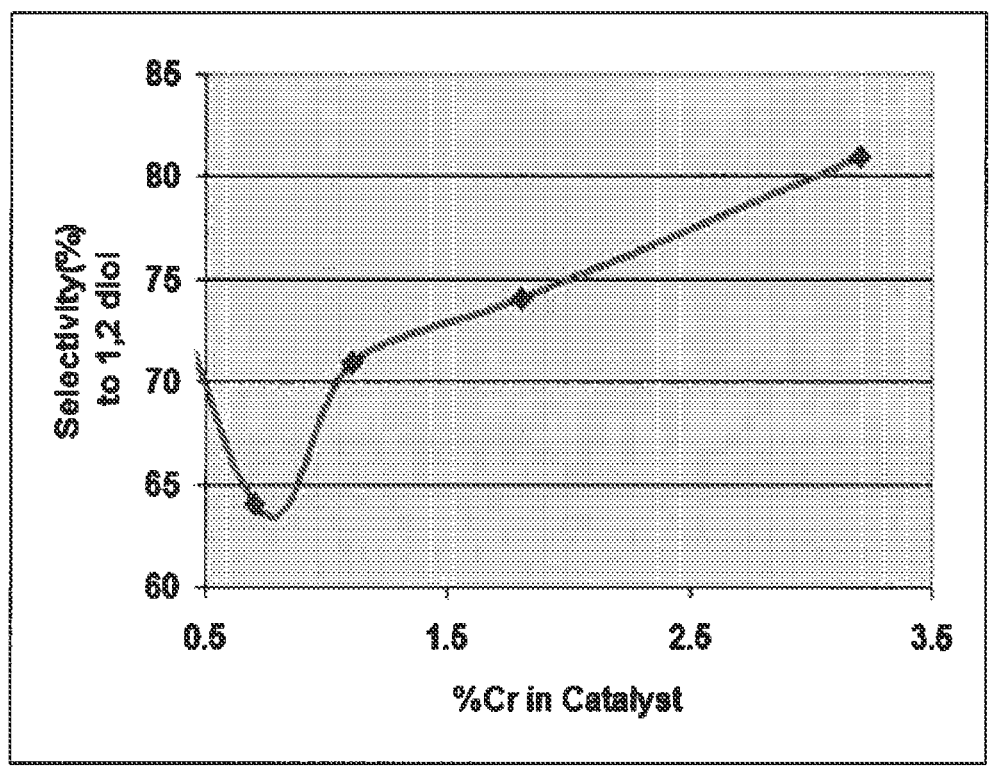
FIG. 5 is a graph illustrating selectivity of the invention for 1,2 propane diol relative to Cr content of the catalyst used in the invention. The data in this figure reflect Stage 2 selectivity data reported for Examples 15-18 in Table 2.

(2) Among the promoted catalysts tested, selectivity for 1,2 PG is best at highest Cr levels within this range of 0.7-3.3% Cr. See FIG. 5.

(3) Metal promotion increases % conversion to levels as high as 80%, higher than for unpromoted catalyst.

Figure 6:
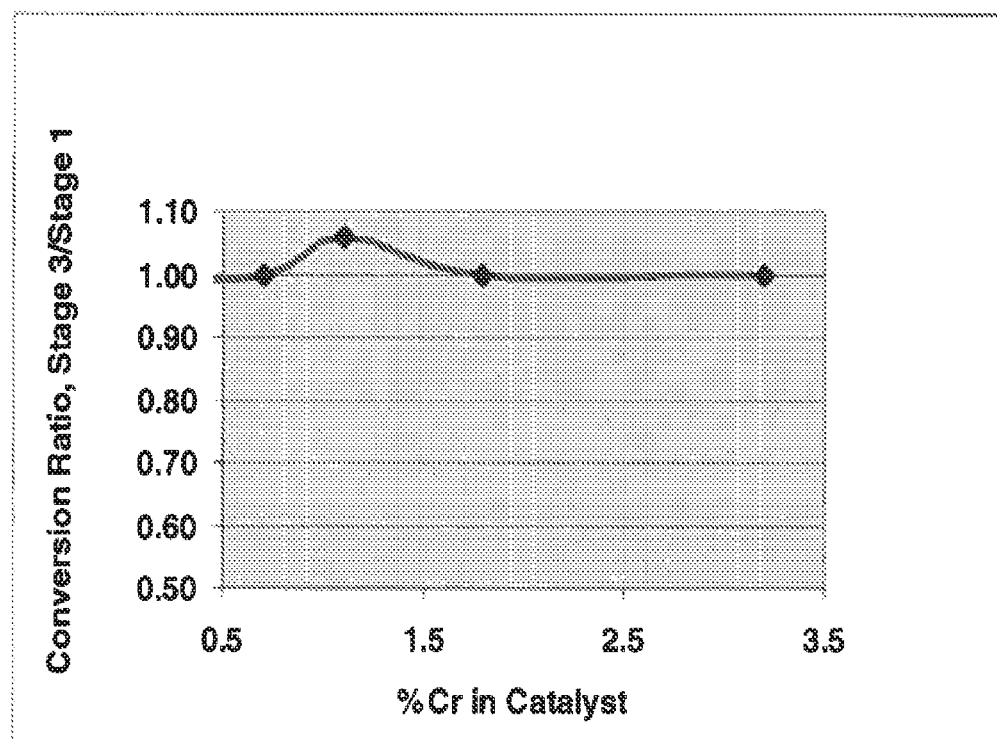
FIG. 6 shows stability of the invention when using transition metal promoted skeletal copper catalysts wherein the transition metal is a component of the alloy used to make the catalyst. The plotted stability data is that reported under "Conv Stage 3/1" for examples 15-18 in Table 2. The stability data therein is a ratio of the invention's conversion after Stage 3 and the invention's conversion after Stage 1, as reported for the same examples.

(4) Catalyst Stability is consistently high for metal, e.g., Cr-promoted catalysts. See FIG. 6.

What is claimed is:

1. A process for producing 1,2-propane diol comprising:
   (a) subjecting glycerol-containing feed stream to hydrogenation conditions in the presence of a skeletal copper catalyst promoted with chromium, wherein the skeletal copper catalyst is prepared from a precursor alloy comprising chromium, and wherein the skeletal copper catalyst comprises 0.5 to 15% by weight chromium (b) recovering an organic product from the same comprising 1,2-propane diol.

2. A process according to claim 1 wherein the precursor alloy comprises chromium in an amount of up to 10% by weight of the total precursor alloy.

3. A process according to claim 1 wherein the skeletal copper catalyst is prepared from a precursor alloy comprising at least copper, chromium, and aluminum that has been leached of at least 40% of the aluminum originally present in the alloy.

4. A process according to claim 1 wherein the skeletal copper catalyst is prepared from a precursor alloy comprising at least copper, chromium, and aluminum that has been leached of at least 50% of the aluminum originally present in the alloy.

5. A process according to claim 2 wherein the skeletal copper catalyst comprises 0.5 to 5% by weight chromium.

6. A process according to claim 1, wherein the recovered organic product comprises less than 2% by weight 1,2-ethane diol.

7. A process according to claim 1 wherein the glycerol-containing feedstream is introduced as a liquid to a reactor in which the feedstream is subjected to hydrogenation conditions in the presence of a skeletal copper catalyst promoted with chromium and the hydrogenation conditions comprise temperature in the range of 180 to 210° C., and a pressure in the range of 100 psig to 1000 psig.

8. A process according to claim 7 wherein the hydrogenation conditions comprise a temperature in the range of 190 to 200° C. and pressure in the range of 100 to 300 psig.

9. A process according to claim 1 wherein the skeletal copper catalyst is in a fixed bed.

10. A process for producing 1,2-propane diol comprising:
(a) introducing glycerol-containing feedstream as a liquid to a reactor in which the feedstream is subjected to hydrogenation conditions in the presence of a skeletal copper catalyst promoted with chromium, wherein the skeletal copper catalyst is prepared from a precursor alloy comprising chromium, and wherein the skeletal copper catalyst comprises 0.5 to 15% by weight chromium (b) recovering from the same a product comprising 1,2-propane diol.

11. A process according to claim 10 wherein the precursor alloy comprises chromium in an amount of up to 10% by weight of the total precursor alloy.

12. A process according to claim 10 wherein the skeletal copper catalyst is prepared from a precursor alloy comprising at least copper, chromium, and aluminum that has been leached of at least 40% of the aluminum originally present in the alloy.

13. A process according to claim 10 wherein the skeletal copper catalyst is prepared from a precursor alloy comprising at least copper, chromium, and aluminum that has been leached of at least 50% of the aluminum originally present in the alloy.

14. A process according to claim 11 wherein the skeletal copper catalyst comprises 0.5 to 5% by weight chromium.

15. A process according to claim 10, wherein the recovered product comprises less than 2% by weight 1,2-ethane diol.

16. A process according to claim 14, wherein the recovered product comprises less than 2% by weight 1,2-ethane diol.

17. A process according to claim 10 wherein the hydrogenation conditions comprise temperature in the range of 190° C. to 210° C. and a pressure in the range of 100 to 1000 psig.

18. A process according to claim 10 wherein the skeletal copper catalyst is in a fixed bed.

* * * * *